United States Patent [19]

Mederski et al.

[11] Patent Number: 5,401,738
[45] Date of Patent: Mar. 28, 1995

[54] BENZIMIDAZOLE COMPOUNDS

[75] Inventors: Werner Mederski, Erzhausen; Dieter Dorsch, Ober-Ramstadt; Norbert Beier, Reinheim; Pierre Schelling, Mühltal; Ingeborg Lues, Darmstadt; Klaus-Otto Minck, Ober-Ramstadt; Mathias Osswald, Zwingenberg, all of Germany

[73] Assignee: Merck Patent Gesellschaft mit Beschrankter, Darmstadt, Germany

[21] Appl. No.: 75,247

[22] Filed: Jun. 11, 1993

[30] Foreign Application Priority Data

Jun. 13, 1992 [DE] Germany .................. 42 19 409.1
Nov. 7, 1992 [DE] Germany .................. 42 37 656.4

[51] Int. Cl.⁶ .................. A61K 31/50; C07D 403/14; C07D 405/14; C07D 417/14
[52] U.S. Cl. .................. 514/222.5; 514/254; 544/8; 544/238; 544/239
[58] Field of Search .................. 544/8, 238, 239; 514/222.5, 254

[56] References Cited

U.S. PATENT DOCUMENTS

| | | | |
|---|---|---|---|
| 4,026,891 | 5/1977 | Austel et al. I | 544/238 |
| 4,699,909 | 10/1987 | Hauel et al. I | 514/254 |
| 4,880,804 | 11/1989 | Carini et al. | 548/125 |
| 4,923,869 | 5/1990 | Prücher et al. | 514/253 |
| 4,957,920 | 9/1990 | Mörsdorf et al. | 514/252 |
| 5,026,705 | 6/1991 | Prucher et al. | 544/8 |
| 5,039,675 | 8/1991 | Mörsdorf et al. | 514/252 |
| 5,135,932 | 8/1992 | Hauel et al. II | 514/253 |

FOREIGN PATENT DOCUMENTS

| | | | |
|---|---|---|---|
| 2051705 | 12/1991 | Canada . | |
| 0196005 | 10/1986 | European Pat. Off. | 544/230 |
| 0240026 | 10/1987 | European Pat. Off. | 544/238 |
| 0468470 | 7/1991 | European Pat. Off. . | |
| 0467248 | 1/1992 | European Pat. Off. | 544/238 |
| 3728244 | 3/1989 | Germany | 544/238 |

OTHER PUBLICATIONS

Chiu et al., The Journal of Pharmacology and Experimental Therapeutics, vol. 250, No. 3, pp. 867–874 (May 22, 1989).

Wong et al., The Journal of Pharmacology and Experimental Therapeutics, vol. 252, No. 2, pp. 719–725 (Oct. 26, 1989).

*Primary Examiner*—Floyd D. Higel
*Attorney, Agent, or Firm*—Millen, White, Zelano & Branigan

[57] ABSTRACT

Benzimidazole compounds of the formula I

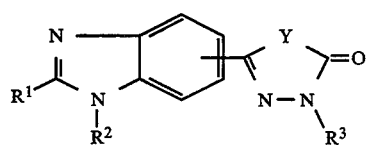

and salts thereof, exhibit antagonistic properties toward angiotensin II and can be used for the treatment of hypertension, aldosteronism, cardiac insufficiency and an increased intraocular pressure, as well as disturbances of the central nervous system.

24 Claims, No Drawings

BENZIMIDAZOLE COMPOUNDS

SUMMARY OF THE INVENTION

The invention relates to new benzimidazole derivatives of the formula I

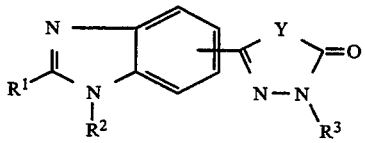

I wherein $R^1$ is H, A, $C_pH_{2p}$-($C_{3-7}$-cycloalkyl), OA, SA, Ar or $Het^1$, $R^2$ and $R^3$ are in each case

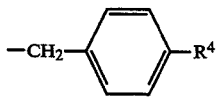

(1)

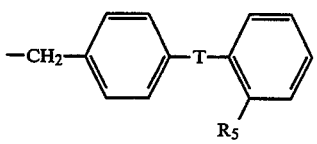

(2)

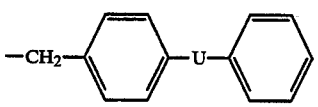

(3)

(4) —$C_{1-10}$-alkyl, —$C_nH_{2n}$—COOR, —$C_nH_{2n}$—CN, —$C_mH_{2m}$—Ar, —$C_m$-$H_{2m}Het^2$, —$C_nH_{2n}$—1H-5-tetrazolyl, —$C_nH_{2n}$—CH=CH—Ar, —$C_nH_{2n}$—CO—N(R)$_2$, —$C_mH_{2m}$—CO—R, —$C_mH_{2m}$—CO—Ar, —$C_nH_{2n}$—O—CON(R)$_2$ or —$C_nH_{2n}$—N—R—CO—N(R)$_2$, or (5) H, Y is —C(R)$_2$—C(R)$_2$—, —CR=CR— or —C(R)$_2$—S—, the radicals R independently of one another are H or A, $R^4$ is COOR, CN or 1H-5-tetrazolyl, $R^5$ is COOR, CN, NO$_2$, NH$_2$, NHCOCF$_3$, NHSO$_2$CF$_3$ or 1-H-5-tetrazolyl, T is absent or is —NR—CO—, —CO—NR— or —CH=CH—, U is —CH=C(COOR)—, —CH=C(CN)—, —CH=C(1H-5-tetrazolyl)—, —O—CH(COOR)— or —NR—CH(COOR)—, m and p are each 0, 1, 2, 3, 4, 5, 6, 7, 8, 9 or 10, n is 1, 2, 3, 4,.5, 6, 7, 8, 9 or 10, A is alkyl having 1-6 C atoms, Ar is a phenyl or naphthyl group which is unsubstituted or mono- or disubstituted by A, Hal, OH, OA, COOH, COOA, CN, CF$_3$, NO$_2$, NH$_2$, NHA and/or N(A)$_2$, $Het^1$ is an indolyl, 2,3-dihydroindolyl, benzofuryl, 2,3-dihydrobenzofuryl, benzothienyl or 2,3-dihydrobenzothienyl group which is unsubstituted or monosubstituted by A, $C_{1-7}$-alkanoyl or COOA, $Het^2$ is an unsubstituted or substituted five- or six-membered heteroaromatic radical which has 1 to 3 N, O and/or S atoms and can also be fused with a benzene or pyridine ring and Hal is F, Cl, Br or I, with the proviso that 1. Y is only —C(R)$_2$—C(R)$_2$— or —CR=CR— if $R^1$ is other than —$C_pH_{2p}$—($C_{1-3}$-cycloalkyl) and/or if $R^3$ is other than H and 2. at least one of the radicals $R^2$ and $R^3$ has one of the meanings (1), (2) or (3), and their salts.

Similar compounds are known from EP-A1-0 468 470.

An object of the invention is to provide novel compounds with valuable properties, especially compounds which can be used for the preparation of drugs.

Upon further study of the specification and appended claims, further objects and advantages of this invention will become apparent to those skilled in the art.

It has been found that the compounds of formula I and their salts possess very valuable pharmacological properties coupled with a good tolerance. In particular, they exhibit antagonistic properties toward angiotensin II and can therefore be used for the treatment of angiotensin II-dependent hypertension, aldosteronism and cardiac insufficiency, as well as disorders of the central nervous system. These effects can be determined by conventional in vitro or in vivo methods such as those described for example in EP-A1-0 468 470, in U.S. Pat. No.4,880,804 and in WO 91/14367, as well as those described by A. T. Chiu et al., J. Pharmacol. Exap. Therap. 250, 867–874 (1989), and by P. C. Wong et al., ibid. 252, 719–725 (1990; in vivo, on rats).

The compounds of formula I can be used as pharmaceutical active ingredients in human and veterinary medicine, especially for the prophylaxis and/or therapy of cardiac, circulatory and vascular diseases and in particular of hypertonia, cardiac insufficiency and hyperaldosteronism, furthermore of hypertrophy and hyperplasia of the blood vessels and of the heart, angina pectoris, cardiac infarctions, apoplexy, restenoses after angioplasty or bypass operations, arteriosclerosis, increased intraocular pressure, glaucomas, macular degeneration, hyperuricaemia, kidney dysfunctions, for example kidney failure, nephropathia diabetica, retinopathia diabetica, psoriasis, disorders in the female reproductive organs due to angiotensin II, perceptual disorders, for example dementia, amnesia, memory dysfunctions, anxiety conditions, depression and/or epilepsia.

The invention relates to the compounds of formula I and their salts and to a process for the preparation of these compounds and their salts, characterized in that (a) a compound of the formula II

E–Z  II wherein

E is Cl, Br, I, a free OH group or an OH group which has been functionally modified to acquire reactivity and Z is $R^2$ or $R^3$, but not H, is reacted with a compound of the formula III

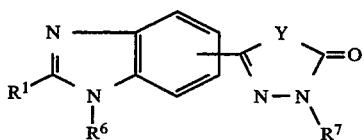

wherein
$R^6$ is $R^2$ (if Z is $R^3$) and
$R^7$ is $R^3$ (if Z is $R^2$), at least one of the radicals $R^6$ and $R^7$ is H, however, and
$R^1$ and Y are as defined in formula I, or
(b) a compound of the formula IV

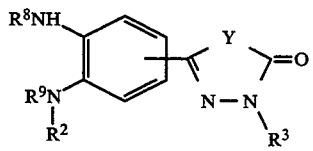

wherein
$R^8$ is $R_1$—CO or H and
$R^9$ is H (if $R^8$ is $R^1$—CO) or $R^1$—CO (if $R^8$ is H), and
$R^1$, $R^2$, $R^3$ and Y are as defined in formula I, is treated with a cyclizing agent, or
(c) to prepare a compound of the formula I wherein T is —NR—CO— or —CO—NR—, a compound of the formula V

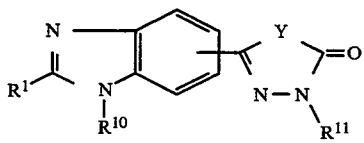

wherein
$R^{10}$ is $R^2$ or

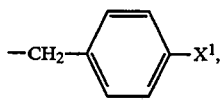

$R^{11}$ is $R^3$ (if $R^{10}$ is

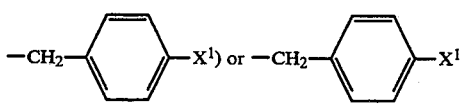

(if $R^{10}$ is $R^2$) and
$X^1$ is $NH_2$ or COOH, and
$R^1$ and Y are as defined in formula I,
or a reactive derivative of this compound, is reacted with a compound of the formula VI

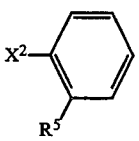

wherein
$X^2$ is COOH (if $X^1$ is $NH_2$) or $NH_2$ (if $X^1$ is COOH) and
$R^5$ is as defined in formula I, or with a reactive derivative of this compound,
or in that a compound of the formula I is freed from one of its functional derivatives by treatment with a solvolyzing or hydrogenolyzing agent, and/or in that one or more radicals $R^2$ and/or $R^3$ in a compound of the formula I are converted into one or more other radicals $R^2$ and/or $R^3$, and/or a compound of the formula I wherein Y is —CHR—CHR— is converted into a compound of the formula I wherein Y is —CR=CR— by treatment with a dehydrogenating agent, and/or a base or acid of the formula I is converted into one of its salts.

Above and below, the radicals or parameters $R^1$ to $R^{11}$, R, T, U, m, n, p, $X^1$, $X^2$, Y, A, At, $Het^1$, $Het^2$, Hal, E and Z are as defined in formulae I to V, unless expressly indicated otherwise.

In the above formulae, A is, in particular, alkyl having 1-6, preferably 1, 2, 3 or 4 C atoms, preferably methyl, or else ethyl, propyl, isopropyl, butyl, isobutyl, sec-butyl or tert-butyl, or else pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

Accordingly, the radical OA is preferably methoxy, or else ethoxy, propoxy, isopropoxy, butoxy, isobutoxy, sec-butoxy or tert-butoxy, and the radical SA is preferably methylthio, or else ethylthio. The group COOA is preferably methoxycarbonyl or ethoxycarbonyl, or else propyloxycarbonyl, isopropyloxycarbonyl, butyloxycarbonyl iso butyloxycarbonyl. The group NHA is preferably methylamino or ethylamino. The group $N(A)_2$ is preferably dimethylamino or diethylamino.

Cycloalkyl is preferably cyclopropyl, furthermore cyclobutyl, cyclopentyl, cyclohexyl or cycloheptyl, but also, for example, 1- or 2-methylcyclopropyl, 1-, 2- or 3-methylcyclopentyl, or 1-, 2-, 3- or 4-methylcyclohexyl.

Hal is preferably F, Cl or Br, or else I.

The radical Ar is preferably an unsubstituted phenyl group, or else preferably a phenyl group monosubstituted in the p-position or monosubstituted in the o- or m-position. Preferred substituents are OA, COOH, COOA and $NO_2$. Accordingly, Ar is preferably phenyl, o-, m- or (especially) p-methoxyphenyl, o-, m- or (especially) p-carboxyphenyl, o-, m- or (especially) p-methoxycarbonylphenyl, o-, m- or (especially) p-ethoxycarbonylphenyl, o-, m- or (especially) p-nitrophenyl, or else preferably o-, m- or (especially) p-aminophenyl, o-, m- or (especially) p-dimethylaminophenyl, o-, m- or (especially) p-diethylaminophenyl, o-, m- or p-tolyl, o-, m- or p-trifluoromethylphenyl, o-, m- or p-hydroxyphenyl, o-, m- or p-fluorophenyl, o-, m- or p-chlorophenyl, o-, m- or p-bromophenyl, o-, m- or p-iodophenyl, o-, m- or p-cyanophenyl, o-, m- or p-methylaminophenyl or 1- or 2-naphthyl.

The radical $Het^1$ is preferably 2,3-dihydro-1-methoxycarbonyl-2-, -3-, -4-, -5-, -6- or -7-indolyl, 2,3-dihydro-1-ethoxycarbonyl-2-, -3-, -4-, -5-, -6- or -7-indolyl. Alternatively, $Het^1$ is also preferably unsubstituted 1-, 2-, 3-, 4-, 5-, 6- or 7-indolyl, 2-, 3-, 4-, 5-, 6- or 7-benzofuryl, 2,3-dihydro-2-, -3-, -4-, -5-, -6- or -7-benzofuryl, 2-, 3-, 4-, 5-, 6- or 7-benzothienyl, 2,3-dihydro-2-, -3-, -4-, -5-, -6- or -7-benzothienyl, it being also possible for these radicals to be substituted by A (preferably methyl), $C_{1-7}$-alkanoyl (preferably acetyl) or COOA (preferably methoxycarbonyl or ethoxycarbonyl) in one of the free positions.

$Het^2$ is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2 -, 3- or 4-pyridyl, 2 -, 4 -, 5- or 6 -pyrimidinyl, or else preferably 1,2,3-triazol-1-, -4- or -5-yl, 1,2,4-triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 2,1,5-thiadiazol-3- or -4-yl, 3-or 4-pyridazinyl, pyrazinyl, 2-, 3-, 4-, 5-, 6or 7-benzofuryl, 2-, 3-, 4-, 5-, 6- or 7-benzothienyl, 1-, 2-, 3-, 4-, 5-, 6-or 7-indolyl, 1-, 2-, 3-, 4-, 5-, 6- or 7-isoindolyl, 1-, 2-, 4- or 5-benzimidazolyl, 1-, 3-, 4 -, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6 - or 7 -benz-2 - 1,3 -oxadiazolyl, 2 -, 3-, 4-, 5-, 6-, 7-or 8-quinolyl, 1-, 3-, 4-, 5-, 6-, 7or 8-isoquinolyl, 3-, 4-, 5-, 6-, 7-or 8-cinnolyl, 2-, 4-, 5-, 6-, 7-or 8-quinazolyl, 1H-1-, -2-, -5-, -6-or -7-imidazo[4,5-b]pyridyl, 3H-2-, -3-, -5-, -6- or -7imidazo[4,5-b]pyridyl, 1H-1-, -2-, -4-, -6- or -7imidazo[4,5-c]pyridyl or 3H-2-, -3-, -4-, -6- or -7imidazo[4,5-c]pyridyl.

The term "$Het^2$" also includes the homologous radicals in which the heteroaromatic ring is substituted by one or more, preferably 1 or 2 A groups, preferably methyl and/or ethyl groups, for example 3-, 4- or 5-methyl-2-furyl, 2-, 4- or 5-methyl-3-furyl, 2,4-dimethyl-3-furyl, 3-, 4- or 5-methyl-2-thienyl, 3-methyl-5-tertbutyl-2-thienyl, 2-, 4- or 5-methyl-3-thienyl, 2- or 3-methyl-1-pyrrolyl, 1-, 3 -, 4 - or 5 -methyl-2 -pyrrolyl, 3,5-dimethyl-4 -ethyl-2 -pyrrolyl, 2-, 4- or 5-methyl- 1-imidazolyl, 4-methyl-5-pyrazolyl, 4- or 5-methyl-3-isoxazolyl, 3- or 5-methyl-4-isoxazolyl, 3- or 4-methyl-5-isoxazolyl, 3,4-dimethyl-5-isoxazolyl, 4- or 5-methyl-2-thiazolyl, 4- or 5-ethyl-2-thiazolyl, 2- or 5-methyl-4-thiazolyl, 2- or 4-methyl-5-thiazolyl, 2,4-dimethyl-5-thiazolyl, 3-, 4-, 5- or 6-methyl-2-pyridyl, 2-, 4-, 5- or 6-methyl-3-pyridyl, 2- or 3-methyl-4-pyridyl, 4-methyl-2-pyrimidinyl, 4,6-dimethyl-2-pyrimidinyl, 2-, 5- or 6-methyl-4-pyrimidinyl, 2,6-dimethyl-4-pyrimidinyl, 3-, 4-, 5-, 6- or 7-methyl-2-benzofuryl, 2-ethyl-3-benzofuryl, 3-, 4-, 5-, 6- or 7-methyl-2-benzothienyl, 3-ethyl-2-benzothienyl, 1-, 2-, 4-, 5-, 6- or 7-methyl-3-indolyl, 1-methyl-5- or 6-benzimidazolyl, 1-ethyl-5- or 6-benzimidazolyl.

The radical T is preferably absent; or else T is preferably —NH—CO—, —N(CH$_3$)—CO—, —CO—NH—, —CO—N—CH$_3$)— or —CH=CH—.

The radical U is preferably —CH=C(CN)— or —CH=C—(1H-5-tetrazolyl)—, or else preferably —CH=C(COOH)—, —CH=C(COOH$_3$)—, —CH=C(COOC$_2$H$_5$)—, —O—CH(COOH)—, —O—CH—(COOCH$_3$)—, —O—CH(COOC$_2$H$_5$)—, —NH—CH(COOH)—, —N(CH$_3$)—CH—(COOH)—, —NH—CH(COOCH$_3$)—, —N(CH$_3$)—CH(COOCH$_3$)—, —NH—CH(COOC$_2$H$_5$) or —N(CH$_3$)—CH—(COOC$_2$H$_5$)—.

The radical Y is preferably —CH(CH$_3$)—CH$_3$)— or —C(CH$_3$)=CH—.

The radicals R independently of one another are preferably H, CH$_3$ or C$_2$H$_5$.

The radical $R^1$ is preferably A or cycloalkyl, especially butyl or cyclopropyl, or else preferably propyl, pentyl or hexyl, or else preferably H, cyclopropylmethyl, p-methoxyphenyl or 2,3-dihydro-1-methoxycarbonyl-indolyl.

The radical $R^2$ is preferably H, 2'-cyano-biphenylyl-4-methyl, 2'-carboxy-biphenylyl-4-methyl, 2'-(1H-5-tetrazolyl)-biphenylyl-4-methyl or p-(2-cyano-2-phenylvinyl)-benzyl.

The radical $R^3$ is preferably H, carboxymethyl, o-, m- or (especially) p-carboxybenzyl, 2'-cyano-biphenylyl-4-methyl, 2'-carboxy-biphenylyl-4-methyl or 2'-(1H-tetrazolyl)-biphenylyl-4-methyl.

The radical $R^4$ is preferably COOH, or else preferably COOCH$_3$, COOC$_2$H$_5$, CN or 1H-5-tetrazolyl.

The radical $R^5$ is preferably COOH, COOCH$_3$, COOC$_2$H$_5$, CN or 1H-5-tetrazolyl.

The parameter m is preferably 0, 1 or 2, the parameter p is preferably 0 or 1, and the parameter n is preferably 1 or 2. The group $C_mH_{2m}$ here is preferably —(CH$_2$)—, especially —CH$_2$— or —CH$_2$CH$_2$—, the group $C_pH_{2p}$ is preferably —(CH$_2$)$_p$—, in particular —CH$_2$—, and the group $C_nH_{2n}$ is preferably —(CH$_2$)$_n$—, especially —CH$_2$— or —CH$_2$CH$_2$—.

The compounds of the formula I can possess one or more chiral centers and can therefore exist in different forms (optically active or optically inactive). Formula I includes all these forms.

Accordingly, the invention relates especially to those compounds of the formula I in which at least one of the said radicals has one of the preferred meanings indicated above. Some preferred groups of compounds can be expressed by the following partial formulae Ia to Id, which correspond to formula I and wherein the radicals not described more precisely are as defined in formula I, but wherein in Ia $R^1$ is H, A, cyclopropyl, p-methoxyphenyl or 2,3-dihydro-1-methoxycarbonyl-indolyl;
in Ib $R^1$ is A;
in Ic $R^2$ is H, 2'-cyano-biphenylyl-4-methyl, 2'-carboxy-biphenylyl-4-methyl, 2'-(1H-5-tetrazolyl)-biphenylyl-4-methyl or p-(2-cyano-2-phenylvinyl)-benzyl;
in Id $R^1$ is A and
$R^2$ is H, 2'-cyano-biphenylyl-4-methyl, 2'-carboxy-biphenylyl-4-methyl, 2'-(1H-5-tetrazolyl)biphenylyl)-4-methyl or p-(2-cyano-2-phenylvinyl)-benzyl.

Compounds which are furthermore preferred are those of the formulae: Ie and Iae, Ibe, Ice and Ide, which correspond to formulae I and Ia, Ib, Ic and Id, but wherein additionally $R^3$ is H, carboxymethyl, carboxybenzyl, 2'-cyanobiphenylyl-4-methyl, 2'-carboxy-biphenylyl-4-methyl or 2'-(1H-5-tetrazolyl)-biphenylyl-4-methyl; If and Iaf, Ibf, Icf and Idf, which correspond to formulae I and Ia, Ib, Ic and Id, but wherein additionally $R^3$ is H; and Ig and Iag, Ibg, Icg and Idg, which correspond to formulae I and Ia, Ib, Ic and Id, but wherein additionally $R^3$ is carboxymethyl.

Especially preferred compounds are all those of the abovementioned formulae in which additionally Y is —CH(CH$_3$)—CH$_2$— or —C(CH$_3$)=CH—.

The compounds of formula I and also the starting materials for their preparation are moreover prepared by methods known per se, such as those described in the literature (for example in the standard works like Houben-Weyl, Methoden der organischen Chemie (Methods of Organic Chemistry), Georg-Thieme-Verlag, Stuttgart, but especially in European Patent Application A2-0 468 470 and U.S. Pat. No. 4,880,804), under reaction conditions which are known and suitable for said reactions, it also being possible to make use of variants known per se, which are not mentioned in greater detail here.

If desired, the starting materials can also be formed in situ, so that they are not isolated from the reaction mixture but immediately reacted further to give the compounds of formula I.

The compounds of formula I can preferably be obtained by reacting compounds of formula II with compounds of formula III.

In the compounds of formula II, E is preferably Cl, Br, I or an OH group which has been functionally modified to acquire reactivity, such as alkylsulfonyloxy having 1–6 C atoms (preferably methylsulfonyloxy) or arylsulfonyloxy having 6–10 C atoms (preferably phenyl- or p-tolyl-sulfonyloxy).

The reaction of II with III is conveniently carried out by first converting III to a salt by treatment with a base, for example with an alkali metal alcoholate such as $CH_3ONa$ or potassium tert-butylate in an alcohol such as $CH_3OH$, in an ether such as tetrahydrofuran (THF) or in an amide such as dimethylformamide (DMF), or with an alkali metal hydride such as NaH or an alkali metal alcoholate in DMF, and then reacting said salt with II in an inert solvent, for example an amide such as DMF or dimethylacetamide, or a sulfoxide such as dimethyl sulfoxide (DMSO), conveniently at temperatures of preferably about $-20°-100°$, especially $10°-30°$. Other suitable bases are alkali metal carbonates such as $Na_2CO_3$ or $K_2CO_3$, or alkali metal hydrogen carbonates such as $NaHCO_3$ or $KHCO_3$.

If a compound of the formula III in which $R^6=R^7=H$ is used, mixtures are as a rule obtained in the reaction with II, these can easily be separated, for example by chromatography. The ratio of the amounts and the nature of the products can be controlled by modifying the reaction conditions. Thus, if equimolar amounts of II and III are employed, the product substituted on the benzimidazole N atom is chiefly formed if an equimolar amount of the base is used; while the product substituted in the 1-position of the pyridazinone or thiopyridazinone ring is chiefly obtained if an excess of base is used.

The compounds of formula I furthermore are obtainable by cyclization of compounds of formula IV. This cyclization is expediently carried out by heating to temperatures of preferably about $80°-180°$, especially $120°-160°$, with polyphosphoric acid, acetic acid or diglyme.

Acid amides of formula I (T=—NR—CO— or —CO—NR—) can also be obtained by reaction of compounds of formula V (or reactive derivatives thereof) with compounds of formula VI (or reactive derivatives thereof).

Suitable reactive derivatives of the carboxylic acids of formulae V and VI ($X^1$ or $X^2$=COOH) are advantageously the corresponding chlorides, bromides or anhydrides. The reaction is conveniently carried out in the presence of an inert solvent, for example a halogenated hydrocarbon such as methylene chloride, chloroform, trichloroethane or 1,2-dichloroethane, or an ether such as THF or dioxane, at temperatures of preferably about $0°-150°$, especially $20°-80°$. If acid halides are reacted, it is recommended to add a base, for example a tertiary amine such as triethylamine, pyridine or 4-dimethylaminopyridine.

A compound of formula I furthermore can be freed from one of its functional derivatives by solvolysis (for example hydrolysis) or hydrogenolysis.

Carboxylic acids of formula I wherein U is —O—CH(COOH), —NH—CH(COOH), —NA—CH(COOH) or —CH=C(COOH) can thus be obtained by hydrolysis of corresponding alkyl esters, for example with NaOH or KOH in aqueous solution, with or without addition of an inert organic solvent, such as methanol, ethanol, THF or dioxane, at temperatures of preferably about $0°-100°$, or by hydrogenolysis of corresponding benzyl esters, for example on Pd-on-charcoal under pressures of preferably about 1-200 bar and at temperatures of preferably about $0°-100°$ in one of the inert solvents mentioned.

It is also possible to prepare a compound which corresponds to formula I but contains a 1H- (or 2H)-5-tetrazolyl group which is functionally modified (protected by a protective group) in the 1-position (or 2-position) instead of a 5-tetrazolyl group by one of the methods described and finally to split off this protective group. Examples of suitable protective groups are: triphenylmethyl, which can be split off with HCl or formic acid in an inert solvent or solvent mixture, for example ether/methylene chloride/methanol; 2-cyanoethyl, which can be split off with NaOH in water/THF; or p-nitrobenzyl, which can be split off with $H_2$/Raney nickel in ethanol (compare EP-A2-0 291 969).

The starting substances, especially those of formulae II and VI, are known in some cases. If they are not known, they can be prepared analogously to known substances by known methods.

Compounds of formula III are obtainable, for example, by reaction of carboxylic acids of the formula $R^1$—COOH with compounds of the formula VII

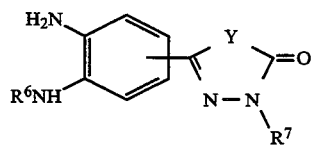

VII in the presence of polyphosphoric acid.

Compounds of formula IV are obtainable, for example, by reaction of compounds of formula VIII

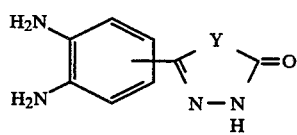

VIII but in which one amino group is protected by an aminoprotective group (for example benzyl, A—O—CO— or benzyloxycarbonyl), with compounds of formula II and subsequent splitting off of the protective group and reaction with acids of the formula $R^1$—COOH or functional derivatives thereof; as a rule, they are not isolated but are formed in situ during the latter reaction. Instead of the acids of the formula $R^1$—COOH, the corresponding aldehydes can also be employed, in the presence of an oxidizing agent such as $Na_2S_2O_5$. 1,3,5-Triazine is also a suitable functional derivative of formic acid ($R^1$=H).

Compounds of formula V can be prepared by reaction of III with benzyl chlorides of the formula $Cl-CH_2-p-C_6H_4-X^3$ (wherein $X^3$ is a protected $NH_2-$ or COOH group) and subsequent splitting off of the protective group.

It is also possible to convert one compound of formula I to another compound of formula I by converting one or more of the radicals $R^2$ and/or $R^3$ to other radicals $R^2$ and/or $R^3$, for example by reducing nitro groups to amino groups (for example by hydrogenation on Raney nickel or Pd-on-charcoal in an inert solvent such as methanol or ethanol), and/or functionally modifying free amino and/or hydroxyl groups, and/or freeing functionally modified amino and/or hydroxyl groups by solvolysis or hydrogenolysis, and/or replacing halogen atoms with CN groups (for example by reaction with copper(I) cyanide), and/or hydrolyzing nitrile groups to COOH groups or to $CONH_2$ groups, or converting nitrile groups to tetrazolyl groups with hydrazoic acid derivatives, for example sodium azide in N-methylpyrrolidone or trimethyltin azide in toluene.

Thus, for example, free amino groups can be acylated in conventional manner with an acid chloride or anhydride, or free hydroxyl and/or NH groups can be alkylated with an unsubstituted or substituted alkyl halide or with aldehydes such as formaldehyde, in the presence of a reducing agent such as $NaBH_4$ or formic acid, conveniently in an inert sovlent such as methylene chloride or THF, and/or in the presence of a base such as triethylamine or pyridine, at temperatures of preferably about $-60°-+30$ °.

If desired, a functionally modified amino and/or hydroxyl group in a compound of formula I can be freed by solvolysis or hydrogenolysis using conventional methods. Thus, for example, a compound of formula I containing a COOA group can be converted to the corresponding compound of formula I containing a COOH group instead. Ester groups can be hydrolyzed for example with NaOH or KOH in methanol, water, water/THF or water/dioxane, at temperatures of preferably about $0°14\ 100°$.

The reaction of nitriles of formula I ($R^2$ or $R^3=-C_nH_{2n}-CN$; or $R^4$ or $R^5=CN$) with hydrazoic acid derivatives leads to tetrazoles of the formula I ($R^2$ or $R^3=-C_nH_{2n}-1H$-5-tetrazolyl; $R^4$ or $R^5=1H$-5-tetrazolyl). It is preferable to use trialkyltin azides, such as trimethyltin azide, in an inert solvent, for example an aromatic hydrocarbon such as toluene, at temperatures of preferably about $20°-150°$, especially $80°-140°$, or sodium azide in N-methylpyrrolidone at temperatures of preferably about $100°-200°$. The trialkyltin group is then split off, either by treatment with hydrochloric acid, for example in dioxane, or with alkali, for example in ethanol/water, or with formic acid, for example in methanol, or by chromatography over a silica gel column, for example with ethyl acetate/methanol.

It is further possible to dehydrogenate a compound of formula I wherein Y is —CHR—CHR—, to a compound of formula I, in which Y is —CR=CR—, preferably with sodium 3-nitrobenzenesulfonate in aqueous-alkaline solution at temperatures of preferably about $0°-100°$. Other suitable dehydrogenating agents are, for example, bromine in acetic acid, $MnO_2$ or $SOCl_2$.

A base of formula I can be converted with an acid to the corresponding acid addition salt, for example by reaction of equivalent amounts of the base and acid in an inert solvent, for example ethanol, and subsequent evaporation. Possible acids for this reaction are especially those which yield physiologically acceptable salts. Thus it is possible to use inorganic acids, for example sulfuric acid, nitric acid, hydrohalic acids such as hydrochloric acid or hydrobromic acid, phosphoric acids such as orthophosphoric acid, and sulfamic acid, as well as organic acids, especially aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-monosulfonic and -disulfonic acids and laurylsulfuric acid. Salts with physiologically unacceptable acids, for example picrates, can be used for isolating and/or purifying the compounds of formula I.

On the other hand, compounds of formula I containing COOH or tetrazolyl groups can be converted with bases (for example sodium or potassium hydroxide or carbonate) to the corresponding metal salts, especially alkali metal or alkaline earth metal salts, or to the corresponding ammonium salts. The potassium salts are particularly preferred.

The novel compounds of formula I and their physiologically acceptable salts can be used for the preparation of pharmaceutical formulations by incorporation into a suitable dosage form together with at least one excipient or adjunct and, if desired, together with one or more other active ingredients. The resulting formulations can be used as drugs in human or veterinary medicine. Possible excipients are organic or inorganic substances which are suitable for enteral (for example oral or rectal) or parenteral administration or for administration in the form of an inhalation spray, and which do not react with the novel compounds, examples being water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; lacquered tablets and capsules with coatings or shells resistant to gastric juices are of special interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant or propellant mixture (for example hydrocarbons such as propane or butane, or fluorocarbons such as heptafluoropropane). It is convenient here to use the active ingredient in micronized form, it being possible for one or more additional physiologically compatible solvents, for example ethanol, to be present. Inhalation solutions can be administered with the aid of conventional inhalers. The novel compounds can also be lyophilized and the resulting lyophilizates used for example for the manufacture of injectable preparations. The indicated formulations can be sterilized and/or can contain adjuncts such as preservatives, stabilizers and/or wetting agents, emulsifiers, salts for influencing the osmotic pressure, buffer substances and colors and/or flavorings. If desired, they can also contain one or more other active ingredients, for example one or more vitamins, diuretics or antiphlogistics.

The substances according to the invention are normally administered analogously to other known, commercially available preparations (e.g., Enalapril and Captopril), but in particularly analogously to the compounds described in U.S. Pat. No. 4,880,804, preferably in doses of about 1 mg–1 g, especially of 50–500 mg per dosage unit. The daily dose is preferably about 0.1–100 mg/kg, especially 1–50 mg/kg of body weight. However, the particular dose for each individual patient depends on a wide variety of factors, for example on the efficacy of the particular compound used, age, body weight, general state of health, sex, diet, time and mode of administration, rate of excretion, drug combination and severity of the particular disease to which the therapy is applied. Oral administration is preferred.

Above and below, all temperatures are given in °C. In the following examples, "conventional working-up" means: water is added if necessary, the pH is adjusted to 2–10 if necessary, depending on the constitution of the end product, extraction is carried out with ethyl acetate or methylene chloride and the organic phase is separated off, dried over sodium sulfate, evaporated and purified by chromatography on silica gel and/or by crystallization. FAB=peak in the mass spectrum obtained by the "Fast Atom Bombardment" method. Rf=Rf value from thin-layer chromatography on silica gel using ethyl acetate/methanol 95:5.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German applications P 42 19 409.1 and P 42 37 656.4, are hereby incorporated by reference.

EXAMPLES

Example 1

(a) 1.12 g of K tert-butylate are added to a solution of 2.84 g of 2-butyl-5-(1,4,5,6-tetrahydro-4-methyl-6-oxo-3-pyridazinyl)-benzimidazole ["IIIa"; m.p. 193°; obtainable by reaction of 3-(3,4-diaminophenyl)-1,4,5,6-tetrahydro-4-methyl-6-pyridazinone with valeric acid and subsequent cyclization with acetic acid analogously to Example 3]in 70 ml of THF, the mixture is stirred at 20° for 30 minutes, and 3.15 g of methyl 4'-bromomethyl-biphenyl-2-carboxylate (IIa) are then added. The mixture is stirred at 20° for 28 hours, evaporated and worked up in the customary manner (ethyl acetate/saturated NH₄Cl solution; chromatography over silica gel with ethyl acetate/methanol 99:1). 2-Butyl-1-(2'-methoxycarbonyl-biphenylyl-4-methyl)-6-(1,4,5,6-tetrahydro-4-methyl-6-oxo-3-pyridazinyl)-benzimidazole (oil) and then 2-butyl-1-(2'-methoxycarbonyl-biphenylyl-4-methyl)-5-(1,4,5,6-tetrahydro-4-methyl-6-oxo-3-pyridazinyl)-benzimidazole (oil) are obtained in succession.

(b) Reaction of the products obtained according to (a) with methyl bromoacetate by the method described under (a) gives 2-butyl-1-(2'-methoxycarbonylbiphenylyl-4-methyl)-6-(1,4,5,6-tetrahydro-1-methoxy-carbonylmethyl-4-methyl-6-oxo-3-pyridazinyl)benzimidazole (oil; FAB 581) and 2-butyl-1-(2'-methoxycarbonylmethyl-4-methyl)-5-(1,4,5,6-tetrahydro-1-methoxycarbonyl-methyl-4-methyl-6-oxo-3-pyridazinyl)-benzimidazole (oil; FAB 581).

(c) A solution of 1 g of the first-mentioned diester obtained according to (b) in 6 ml of 2N aqueous sodium hydroxide solution and 30 ml of dioxane is stirred at 20° for 48 hours. The solution is concentrated, the residue is taken up in water, the mixture is acidified with 1 N hydrochloric acid and the 2-butyl-1-(2'-carboxy-biphenylyl-4-methyl)-5-(1-carboxymethyl-1,4,5,6-tetrahydro-4-methyl-6-oxo-3-pyridazinyl)-benzimidole thus obtained is filtered off; FAB 553; m.p. 155°. Analogous hydrolysis of the second-mentioned diester obtained according to b) gives 2-butyl-1-(2'-carboxy-biphenylyl-4-methyl)-6-(1-carboxymethyl-1,4,5,6-tetrahydro-4-methyl-6-oxo-3-pyridazinyl)benzimidazole; FAB 553; m.p. 143°.

The following compounds are obtained analogously:
from IIIa and 4'-bromomethyl-2-cyano-biphenyl (IIb): 2-butyl-1-(2'-cyano-biphenylyl-4-methyl)-5-(1,4,5,6-tetrahydro-4-methyl-6-oxo-3-pyridazinyl)-benzimidazole and 2-butyl-1-(2'-cyano-biphenylyl-4-methyl)-6-(1,4,5,6-tetrahydro-4-methyl-6-oxo-3-pyridazinyl)-benzimidazole;

from 2-butyl-5-(3,6-dihydro-2-oxo-2H-1,3,4-thiadiazin-5-yl)-benzimidazole (IIIb) and IIa: 2-butyl-1-(2'-methoxycarbonyl-biphenylyl-4-methyl)-5-(3,6-dihydro-2-oxo-2H-1,3,4-thiadiazin-5-yl)-benzimidazole and 2-butyl-1-(2'-methoxycarbonyl-biphenylyl-4-methyl)-6-(3,6-dihydro-2-oxo-2H-1,3,4-thiadiazin-5-yl)benzimidazole;

from IIIb and IIb: 2-butyl-1-(2'-cyano-biphenylyl-4-methyl)-5-(3,6-dihydro-2-oxo-2H-1,3,4-thiadiazin-5-yl)-benzimidazole and 2-butyl-1- (2'-cyano-biphenylyl-4-methyl)-6-(3,6-dihydro-2-oxo-2H-1,3,4-thiadiazin-5-yl)-benzimidazole;

from IIIa and methyl bromoacetate: 2-butyl-1-methoxycarbonylmethyl-5-(1,4,5,6-tetrahydro-4-methyl-6-oxo-3-pyridazinyl)-benzimidazole and 2-butyl-1-methoxycarbonylmethyl-6-(1,4,5,6-tetrahydro-4-methyl-6-oxo-3-pyridazinyl)-benzimidazole;

from 2-butyl-5-(3,6-dihydro-6-methyl-2-oxo-2H-1,3,4-thiadiazin-5-yl)-benzimidazole and IIb: 2-butyl-1-(2'-cyano-biphenylyl-4-methyl)-5-(3,6-dihydro-6-methyl-2-oxo-2H-1,3,4-thiadiazin-5-yl)-benzimidazole and 2-butyl-1-(2'-cyano-biphenylyl-4-methyl)-6-(3,6-dihydro-6-methyl-2-oxo-2H-1,3,4-thiadiazin-5-yl)-benzimidazole.

The following benzimidazoles are obtained analogously: 2-butyl-1-(2'-cyano-biphenylyl-4-methyl)-5-(1,-4,5,6-tetrahydro-1-methoxycarbonylmethyl-4-m ethyl-6-oxo-3-pyridazinyl-2-butyl-1-(2'-cyano-biphenylyl-4-methyl)-6-(1,4,5,6-tetrahydro-1-methoxyc arbonylmethyl-4-methyl-6-oxo-3-pyridazinyl)-2-butyl-1-(2'-cyano-biphenylyl-4-methyl)-5-(3,6-dihydro-1-methoxycarbonylmethyl-2-oxo-2H-1,3,4-thiadiazin-5-yl)and 2-butyl-1-(2'-cyano-biphenylyl-4-methyl)-6-(3,6-dihydro-1-methoxycarbonylmethyl-2-oxo-2H-1,3,4-thiadiazin-5-yl)-;

(with IIb): 2-butyl-5-[1-(2'-cyano-biphenylyl-4-methyl)-1,4,5,6-tetrahydro-4-methyl-6-oxo-3-pyridazinyl]-1-methoxycarbonylmethyl- and 2-butyl-6-[1-(2'-cyanobiphenylyl-4-methyl)-1,4,5,6-tetrahydro-4-methyl-6-oxo-3-pyridazinyl]-1-methoxycarbonylmethyl-;

(with methyl o-bromomethyl-benzoate): 2-butyl-1-(2'-cyano-biphenylyl-4-methyl)-5-(1,4,5,6-tetrahydro-1-o-methoxycarbonylbenzyl-4-methyl-6-oxo-3-pyridazinyl)- and 2-butyl-1-(2'-cyano-biphenylyl-4-methyl)-6-(1,4,5,6-tetrahydro-1-o-methoxycarbonyl-benzyl-4-methyl-6-oxo-3-pyridazinyl)-;

(with N,N-dimethyl-bromoacetamide): 2-butyl-1-(2'-cyano-biphenylyl-4-methyl)-5-(1,4,5,6-tetrahydro-1-N,N-dimethylcarbamoylmethyl-4-methyl-6-oxo-3-pyridazinyl)- and 2-butyl-1-(2'-cyano-biphenylyl-4-methyl)-6-(1,4,5,6-tetrahydro-1-N,N-dimethylcarbamoylmethyl-4-methyl-6-oxo-3-pyridazinyl)-.

Example 2

2.8 g of K tert-butylate are added to a suspension of 2.84 g of IIIa in 60 ml of THF, the mixture is stirred at 20° for 30 minutes, 2.72 g of IIb are added, and the mixture is stirred at 20° for a further 48 hours. After customary working up (saturated NH$_4$Cl solution/methylene chloride), 2-butyl-5-[1-(2'-cyano-biphenylyl-4-methyl)-1,4,5,6-tetrahydro-4-methyl-6-oxo-3-pyridazinyl]-benzimidazole is obtained.

2-Butyl-5-[1,4,5,6-tetrahydro-1-(2'-methoxycarbonyl-biphenyl-4-methyl)-4-methyl-6-oxo-3-pyridazinyl]-benzimidazole is obtained analogously with IIa.

The following 2-(4-methoxyphenyl)-benzimidazoles are obtained analogously from 2-(4-methoxyphenyl)-5-(1,4,5,6-tetrahydro-4-methyl-6-oxo-3-pyridazinyl)-benzimidazole:

with IIb: 5-[1-(2'-cyano-biphenylyl-4-methyl)-1,4,5,6-tetrahydro-4-methyl-6-oxo-3-pyridazinyl]- and with IIa: 5-[1-(2'-methoxycarbonyl-biphenylyl-4-methyl)-1,4,5,6-tetrahydro-4-methyl-6-oxo-3-pyridazinyl]-.

Example 3

(a) A solution of 4.09 g of 3-(3,4-diaminophenyl)-1-(2'-cyano-biphenylyl-4-methyl)-1,4,5,6-tetrahydro-4-methyl-pyridazin-6-one ["D"; oil; obtainable from 3-(3,4-diaminophenyl)-1,4,5,6-tetrahydro-4-methyl-pyridazin-6-one and IIb in the presence of K tertbutylate in DMF at 20° ], 1.02 g of valeric acid, 1.94 g of N-(3-dimethylaminopropyl)-N'-ethyl-carbodiimide, 1.40 g of 1-hydroxybenzotriazole and 1.12 ml of N-methylmorpholine in 100 ml of DMF is stirred at 20° for 18 hours. It is poured into saturated Na$_2$CO$_3$ solution, the residue is dissolved in 135 ml of acetic acid and the solution is heated at 70° for 18 hours. It is evaporated and the residue is chromatographed on silica gel (methylene chloride/methanol 97:3) to give 2-butyl-5-[1-(2'-cyano-biphenylyl-4-methyl)-1,4,5,6-tetrahydro-4-methyl-6-oxo-3-pyridazinyl]-benzimidazole, m.p.70°.

The following 5-[1-(2'-cyano-biphenylyl-4-methyl)-1,4,5,6-tetrahydro-4-methyl-6-oxo-3-pyridazinyl]benzimidazoles are obtained analogously:
with acetic acid: 2 -methyl-
with propionic acid: 2-ethyl-
with butyric acid: 2-propyl-
with isovaleric acid: 2 -isobutyl-
with hexanoic acid: 2 -pentyl-
with heptanoic acid: 2 -hexyl-
with benzoic acid: 2 -phenyl-
with 4-methoxybenzoic acid: 2-( 4-methoxyphenyl )-, m.p. 191°
with isonicotinic acid: 2-(4-pyridyl)- and with 1-methoxycarbonyl-indoline-5-carboxylic acid: 2-(1-methoxycarbonyl-5-indolinyl]-, FAB 595.

(b) A suspension of 475 mg of the compound obtained according to (a) and 620 mg of trimethyltin azide in 50 ml of toluene is boiled for 4 days and evaporated. The residue is chromatographed over silica gel (methylene chloride/methanol 9:1). This gives 2-butyl-5-[1-(2'-(1H-5-tetrazolyl)-biphenylyl-4-methyl)-1,4,5,6-tetrahydro-4-methyl-6-oxo-3-pyridazinyl]-benzimidazole, m.p. 137°.

The following 5-[1-(2'-(1H-5-tetrazolyl)-biphenylyl-4-methyl)-1,4,5,6-tetrahydro-4-methyl-6-oxo-3pyridazinyl]-benzimidazoles are obtained analogously:
2-methyl-
2-ethyl-
2-propyl-
2-isobutyl-
2-pentyl-
2-hexyl-
2-phenyl-
2-(4-methoxyphenyl)-, m.p. 150°.
2-(4-pyridyl)- and
2-(1-methoxycarbonyl-5-indolinyl)-, m.p. 209° .

Example 4

Analogously to Example 3 (a), 3-(3,4-diaminophenyl)-1,4,5,6-tetrahydro-1-(4-methoxycarbonyl-benzyl)-4-methyl-pyridazin-6-one [obtainable from 3-(3,4-diaminophenyl)-1,4,5,6-tetrahydro-4-methyl-pyridazin-6-one and methyl 4-bromomethyl-benzoate]and valeric acid yield 2-butyl-5-[1,4,5,6-tetrahydro-1-(4-methoxycarbonyl-benzyl)-4-methyl-6-oxo-3-pyridazinyl]-benzimidazole, FAB 433.

3-(3,4-Diaminophenyl)-1, 4,5,6-tetrahydro-1-(2'-methoxycarbonyl-biphenylyl-4-methyl)-4-methyl-pyridazin-6-one [which can be prepared from 3-(3,4-diaminophenyl)-1,4,5,6-tetrahydro-4-methyl-pyridazin-6-one and methyl 4'-bromomethyl-biphenyl-2-carboxylate]and valeric acid analogously give 2-butyl-5-[1,4,5,6-tetrahydro-1-(2'-methoxycarbonyl-biphenylyl-4-methyl)-4-methyl-6-oxo-3pyridazinyl]-benzimidazole, FAB 509.

Example 5

A solution of 0.30 g of 1,3,5-triazine and 4.09 g of "D" (compare Example 3 (a)) in 20 ml of DMF is heated at 140° for 18 hours. The mixture is worked up in the customary manner (water/ethyl acetate; chromatography with ethyl acetate/methanol 95:5) to give 5-[1-(2'-cyanobiphenylyl-4-methyl)-1,4,5,6-tetrahydro-4-methyl-6-oxo-3-pyridazinyl]-benzimidazole, FAB 420.

Example 6

A mixture of 3.89 g of 1-p-aminobenzyl-2-butyl-5-(1,4,5,6-tetrahydro-4-methyl-6-oxo-3-pyridazinyl)benzimidazole [obtainable by reaction of 2-butyl-5-(1,4,5,6-tetrahydro-4-methyl-6-oxo-3-pyridazinyl)-benzimidazole with p-nitrobenzyl bromide to give the 1-p-nitrobenzyl derivative and subsequent hydrogenation], 1.5 g of phthalic anhydride and 40 ml of CHCl$_3$ is stirred at 20° for 16 hours. Customary working up gives 2-butyl-1-[4-(2-carboxybenzamido)-benzyl]-5-1,4,5,6-tetrahydro-4-methyl-6-oxo-3-pyridazinyl)-benzimidazole.

Example 7

A mixture of 4.18 g of 2-butyl-1-(4-carboxybenzyl)-5-(1,4,5,6-tetrahydro-4-methyl-6-oxo-3-pyridazinyl)-benzimidazole [obtainable by reaction of IIIa with methyl 4-bromomethyl-benzoate to give the 1-(4-methoxycarbonylbenzyl) compound and subsequent hydrolysis], 12 g of SOCl$_2$ and 35 ml of CHCl$_3$ is dried for 6 hours and evaporated. The resulting crude acid chloride is freed from residues of SOCl₂ by dissolving several times in toluene and evaporating the solution, and is dissolved in 80 ml of THF. This solution is added dropwise to a solution of 1.37 g of anthranilic acid and 0.8 g of NaOH in 100 ml of water, and the mixture is stirred for 24 hours and acidified to pH 5 with HCl. Customary working up gives 2-butyl-1-[4-(2-carboxyanilino-carbonyl)-benzyl]-5-(1,4,5,6-tetrahydro-4-methyl-6-oxo-3-pyridazinyl)-benzimidazole.

Example 8

1 g of 2-butyl-5-[1,4,5,6-tetrahydro-4-methyl-6-oxo-1-(2'-(2-triphenylmethyl-2H-5-tetrazolyl)-biphenylyl-4-methyl)-3-pyridazinyl]-benzimidazole [obtainable from IIIa and 4-bromomethyl-2'-(2-triphenylmethyl-2H-5-tetrazolyl)-biphenyl] is dissolved in 60 ml of 4N HCl in dioxane, and the solution is stirred at 20° for 16 hours. Customary working up gives 2-butyl-5-[1,4,5,6-tetrahydro-4-methyl-6-oxo-1-(2'-(1H-5-tetrazolyl)-biphenylyl-4-methyl)-3-pyridazinyl]-benzimidazole, m.p. 70°.

Example 9

A solution of 1 g of 1-(2'-benzyloxycarbonylbiphenylyl-4-methyl)-5-(1-benzyloxycarbonyl-1,4,5,6-tetrahydro-4-methyl-6-oxo-3-pyridazinyl)-2-butyl-benzimidazole [obtainable by reaction of IIIa with benzyl 4'-bromomethyl-biphenyl-2-carboxylate to give 1-(2'-benzyloxycarbonyl-biphenylyl-4-methyl)-2-butyl-5-(1,4,5,6-tetrahydro-4-methyl-6-oxo-3-pyridazinyl)-benzimidazole and reaction with benzyl bromoacetate] in 25 ml of isopropanol is hydrogenated over 0.5 g of 5% Pd-on-charcoal at 20° under 1 bar until the calculated amount of H₂ has been absorbed. The catalyst is filtered off and the filtrate is evaporated to give 2-butyl-1-(2'-carboxybiphenylyl-4-methyl)-5-(1-carboxymethyl-1,4,5,6-tetrahydro-4-methyl-6-oxo-3-pyridazinyl)-benzimidazole; m.p. 155°.

Example 10

Analogously to Example 3 (b), the corresponding abovementioned (2'-cyano-biphenylyl-4-methyl)derivatives give the following 1-[2'-(1H-5-tetrazolyl)-biphenylyl-4methyl]-benzimidazoles: 2-butyl-5-(1,4,5,6-tetrahydro-1-methoxycarbonylmethyl-4-methyl-6-oxo-3-pyridazinyl)-2-butyl-6-(1,4,5,6-tetrahydro-1-methoxycarbonylmethyl-4-methyl-6-oxo-3-pyridaziny l)-2-butyl-5-(3,6-dihydro-2-oxo-2H-1,3,4-thiadiazin-5-yl)-2-butyl-6-(3,6-dihydro-2-oxo-2H-1,3,4-thiadiazin-5-yl)-2-butyl-5-(3,6-dihydro-1-methoxycarbonylmethyl-2-oxo-2H-1,3,4-thiadiazin-5-yl)-2-butyl-6-(3,6-dihydro-1-methoxycarbonylmethyl-2-oxo-2H-1,3,4-thiadiazin-5-yl)-2-butyl-5-(3,6-dihydro-6-methyl-2-oxo-2H-1,3,4-thiadiazin-5-yl)-2-butyl-6-(3,6-dihydro-6-methyl-2-oxo-2H-1,3,4-thiadiazin-5-yl)-2-butyl-5-(1,4,5,6-tetrahydro-1-o-methoxycarbonylbenzyl-4-methyl-6-oxo-3-pyridazinyl)-2-butyl-6-(1,4,5,6-tetrahydro-1-o-methoxycarbonylbenzyl-4-methyl-6-oxo-3-pyridazinyl)-2-butyl-5-(1,4,5,6-tetrahydro-1-N,N-dimethylcarbamoyl-methyl-4-methyl-6-oxo-3-pyridazinyl)- and 2-butyl-6-(1,4,5,6-tetrahydro-1-N,N-dimethylcarbamoylmethyl-4-methyl-6-oxo-3-pyridazinyl)-, FAB 606, and the following [1,4,5,6-tetrahydro-4-methyl-6-oxo-1-(2'-(1H-5-tetrazolyl)-biphenylyl-4-methyl)-3-pyridazinyl]-benzimidazoles: 5-, m.p. 175° 2-butyl-1-methoxycarbonylmethyl-5- and 2-butyl-1-methoxycarbonylmethyl-6-.

Example 11

Analogously to Example 1 (c), the following benzimidazoles are obtained by hydrolysis of the corresponding abovementioned methyl esters: 2-butyl-5-[1-(4-carboxybenzyl)-1,4,5,6-tetrahydro-4-methyl-6-oxo-3-pyridazinyl]-, m.p. 134°; FAB 418 2-butyl-5-[1-(2'-carboxy-biphenylyl-4-methyl)-1,4,5,6-tetrahydro-4-methyl-6-oxo-3-pyridazinyl]-, FAB 495; tetrahydrate, m.p. 145° 2-butyl-5-(1-carboxymethyl-1, 4,5,6-tetrahydro-4-methyl-6-oxo-3-pyridazinyl)-1-[2'-(1H-5-tetrazolyl)-biphenylyl-4-methyl]-, m.p. >300°, FAB 577 2-butyl-6-(1-carboxymethyl-1,4,5,6-tetrahydro-4-methyl-6-oxo-3-pyridazinyl)-1-[2'-(1H-5-tetrazolyl)-biphenylyl-4-methyl]-, FAB 577 2-butyl-5-(1-carboxymethyl-3,6-dihydro-2-oxo-2H-1,3,4-thiadiazin-5-yl)-1-[2'-(1 H-5-tetrazolyl)-biphenylyl-4-methyl]-2-butyl -6-(1-carboxymethyl-3,6-dihydro-2-oxo-2H-1,3,4-thiadiazin-5-yl)-1-[2'-(1H-5-tetrazolyl)-biph enylyl-4-methyl]-2-butyl-1-carboxymethyl-5-[1,4,5,6-tetrahydro-4-methyl-6-oxo-1-(2'-(1H-5-tetrazolyl)-biph enylyl-4-methyl)]-3-pyridazinyl-2-butyl-1-carboxymet hyl-6-[1,4,5,6-tetrahydro-4-methyl-6-oxo-1-(2'-(1H-5-tetrazolyl)-biphenylyl-4-methyl)]-3-p yridazinyl-2-butyl-5-(1-o-carboxybenzyl-1,4,5,6-tet rahydro-4-methyl-6-oxo-3-pyridazinyl)-1-[2'-(1H-5-tetrazolyl)-biphenylyl-4-methyl]- and 2-butyl-6-(1-o-carboxybenzyl, 4,5,6-tetrahydro-4-methyl-6-oxo-3-pyridazinyl)-1-[2'-(1H-5-tetrazolyl)-biphenylyl-4-methyl]-.

Example 12

A solution of 552 mg of 2-butyl-1-(2'-carboxybiphenylyl-4-methyl)-5-(1-carboxymethyl-1,4,5,6-tetrahydro-4-methyl-6-oxo-3-pyridazinyl)-benzimidazole and 240 mg of Na 3-nitrobenzenesulfonate in 5.5 ml of water and 4.5 ml of 1N NaOH is boiled for 1 hour and evaporated. Chromatography of the residue over silica gel (ethyl acetate/methanol 1:1) gives 2-butyl-1-(2'-carboxybiphenylyl-4-methyl)-5-(1-carboxymethyl1,6-dihydro-4-methyl-6-oxo-3-pyridazinyl) -benzimidazole; FAB 551; m.p. >300°.

The following benzimidazoles are obtained analogously by dehydrogenation of the corresponding 1,4,5,6-tetrahydro-6-oxo-3-pyridazinyl derivatives: 2-butyl-1-(2'-carboxy-biphenylyl-4-methyl)-6-(1-carboxymethyl-1,6-dihydro-4-methyl-6-oxo-3-pyridazinyl)-, FAB 551; m.p.>300° 2-butyl-5-[1-(2'-cyano-biphenylyl-4-methyl)1,6-dihydro-4-methyl-6-oxo-3-pyridazinyl]-, FAB474; trihydrate, m.p. 238°; 2-butyl-5-[1,6-dihydro-4-methyl-6-oxo-1-(2'-(1H-5-tetrazolyl)-biphenylyl-4-methyl)-3-pyridazinyl]-5-[1,6-dihydro-4-methyl-6-oxo-1-(2'-(1H-5-tetrazolyl)-b iphenylyl-4-methyl)-3-pyridazinyl]-2-p-methoxypheny l-5-[1,6-dihydro-4-methyl-6-oxo-1-(2'-(1H-5-tetraz olyl)-biphenylyl-4-methyl)-3-pyridazinyl]-2-(2,3 -dihydro-1-methoxycarbonyl-5-indolyl)-5-[1,6-dihydro-4-methyl-6-oxo-1-(2'-(1H-5-tetrazolyl)-biphenylyl-4-methyl)-3-pyridazinyl]-2-butyl-5-[1-(2'-carboxy-biphenylyl-4-methyl)1, 6-dihydro-4-methyl-6-oxo-3-pyridazinyl]-, m.p. 168° 2-butyl-5-[1-(4-carboxybenzyl)1, 6-dihydro-4-methyl-6-oxo-3-pyridazinyl]-, FAB 416; pentahydrate, m.p. 158° 2-butyl-5-(1-carboxyme thyl1,6-dihydro-4-methyl-6-oxo-3-pyridazinyl)-1-[2'-(1H-5-tetrazolyl)-biphenylyl-4methyl]-2-butyl-6-(1-carboxymethyl1,6-dihydro-4-methyl-6-oxo-3-pyridazinyl)-1-[2'-(1H-5-tetrazolyl)-biphenylyl-4me thyl]-, FAB575;m.p.>300° 2-butyl-1-carboxymeth yl-5-[1,6-dihydro-4-methyl-6-oxo-1-[2'-(1H-5-tetra
zolyl)-biphenylyl-4-methyl)]-2-butyl-1-carboxy
methyl-6-[1,6-dihydro-4-methyl-6-oxo-1-(2'-(1H-
-5-tetrazolyl)-biphenylyl-4-methyl)]-2-butyl-5-(1-o-ca
rboxybenzyl1,6-dihydro-4-methyl-6-oxo-3-pyridazin
yl)-1-[2'-(1H-5-tetrazolyl)-biphenylyl-4methyl]-2-butyl
-6-(1-o-carboxybenzyl1,6-dihydro-4-methyl-6-oxo-3-
pyridazinyl)-1-[2'-(1H-5-tetrazolyl)-biphenylyl-4me-
thyl]-2-butyl-5-(1-N,N-dimethylcarbamoylmethyl1,6-
dihydro-4-methyl-6-oxo-3-pyridazinyl)-1-[2'-(1H-5-tet-
razolyl)biphenylyl-4-methyl]- and 2-butyl-6-(1-N,N-
dimethylcarbamoylmethyl1,6-dihydro-4-methyl-6-oxo-
3-pyridazinyl)-1-[2'-(1H-5-tetrazolyl)biphenylyl-4-
methyl]-.

Example 13

A solution of 4.09 g of "D" (compare Example 3 (a)),
1.7 g of anisaldehyde and 2.5 g of $Na_2S_2O_5$ in 60 ml of
DMF is boiled for 3 hours. Water is added. The precipi-
tate is filtered off and dried. This gives 5-[1-(2'-cyano-
biphenylyl-4-methyl)-1, 4,5,6-tetrahydro-4-methyl-6-
oxo-3-pyridazinyl]-2-(4-methoxyphenyl)-ben-
zimidazole, m.p. 191°; FAB 526.

Analogously, "D" and 1-methoxycarbonyl-5-for-
mylindoline (m.p. 103°; which can be prepared by reac-
tion of indoline with methyl chloroformate in methy-
lene chloride in the presence of pyridine to give 1-
methoxycarbonylindoline and subsequent reaction with
1,1-dichloromethyl methyl ether/$TiCl_4$ in methylene
chloride) give 5-[1-(2'-cyano-biphenylyl-4-methyl)1,
4,5,6-tetrahydro-4-methyl-6-oxo-3-pyridazinyl]-2-(1-
methoxycarbonyl-5-indolinyl)benzimidazole, FAB 595.

Example 14 a) Analogously to Example 1 a), but in DMF (instead
of
THF), 2-cyclopropyl-5-(1,4,5,6-tetrahydro-4-methyl-
6-oxo-3-pyridazinyl)benzimidazole [m.p. 287°; obtain-
able by reaction of 3-(3,4-diaminophenyl)-1,4,5,6-tet-
rahydro-4-methyl-6-pyridazinone with cyclo-
propanecarboxylic acid and subsequent cyclization
using acetic acid analogously to Example 3] and II b
give, after conventional work-up (ethyl acetate; chro-
matography on silica gel using ethyl acetate/methanol
96:4), first 1-(2'-cyano-4-biphenylylmethyl)-2-cyclopro-
pyl-6-(1,4,5,6-tetrahydro-4-methyl-6-oxo-3-
pyridazinyl)benzimidazole (Rf 0.50), then 1-(2'-cyano-
4-biphenylylmethyl)-2-cyclopropyl-5-(1,4,5,6-tetrahy-
dro-4-methyl-6-oxo-3-pyridazinyl)benzimidazole (Rf
0.65; both yellowish oils).

b) Analogously to Example 3 b), the two compounds
mentioned above with trimethyltin azide give 2-cyclo-
propyl-6-(1,4,5,6-tetrahydro-4-methyl-6-oxo-3-
pyridazinyl)-1-[2'-(1H-5-tetrazolyl)-4-biphenylylme-
thyl]benzimidazole (dihydrates, m.p. 216°) and 2-cyclo-
propyl-5-(1,4,5,6-tetrahydro-4-methyl-6-oxo-3-
pyridazinyl)-1-[2'-(1H-5-tetrazolyl)-4-biphenylylme-
thyl]benzimidazole (monohydrate, m.p. 265°).

c) Analogously to Example 12, the two compounds
mentioned above with Na 3-nitrobenzenesulfonate
(boiling for 4 hours in 0.5N aqueous NaOH) give 2-
cyclopropyl-6-(1,6-dihydro-4-methyl-6-oxo-3-
pyridazinyl)-1-[2'-(1H-5-tetrazolyl)-4-biphenylylme-
thyl]benzimidazole (monohydrate, m.p. 225°) and
2-cyclopropyl-5-(1,6-dihydro-4-methyl-6-oxo-3-
pyridazinyl)-1-[2'-(1H-5-tetrazolyl)-4-biphenylylme-
thyl]benzimidazole (tetrahydrates, m.p. 260°).

Example 15 a) Analogously to Example 1 a), but in DMF (instead
of THF), 2-cyclopropylmethyl-5-(1,4,5,6-tetrahydro-4-
methyl-6-oxo-3-pyridazinyl)benzimidazole [obtainable
by reaction of 3-(3,4-diaminophenyl)1, 4,5,6-tetrahydro-
4-methyl-6-pyridazinone with cyclopropylacetic acid
and subsequent cyclization using acetic acid analo-
gously to Example 3] and II b give, after conventional
work-up (ethyl acetate; chromatography on silica gel
using ethyl acetate/methanol 96:4), first 1-(2'-cyano-4-
biphenylylmethyl)-2-cyclopropylmethyl-6-(1,4,5,6-tet-
rahydro-4-methyl-6-oxo-3pyridazinyl)benzimidazole,
then 1-(2'-cyano-4-biphenylylmethyl)-2-cyclopropyl-
methyl-5-(1,4,5,6-tetrahydro-4-methyl-6-oxo-3-
pyridazinyl)benzimidazole.

b) Analogously to Example 3 b), the two compounds
mentioned above with trimethyltin azide give 2-cyclo-
propylmethyl-6-(1,4,5,6-tetrahydro-4-methyl-6-oxo-3-
pyridazinyl)-1-[2'-(1H-5-tetrazolyl)-4-biphenylylme-
thyl]benzimidazole and 2-cyclopropylmethyl-5-(1,4,5,6-
tetrahydro-4-methyl-6-oxo-3-pyridazinyl)1-[2'-(1H-5-
tetrazolyl)-4-biphenylylmethyl]benzimidazole.

c) Analogously to Example 12, the two compounds
mentioned above with Na 3-nitrobenzenesulfonate
(boiling for 4 hours in 0.5N aqueous NaOH) give 2cy-
clopropylmethyl-6-(1,6-dihydro-4-methyl-6-oxo-
3pyridazinyl)-1-[2'-(1H-5-tetrazolyl)-4-biphenylylme-
thyl]benzimidazole and 2-cyclopropylmethyl-5-(1,6-
dihydro-4-methyl-6-oxo-3-pyridazinyl)-1-[2'-(1H-5-tet-
razolyl)-4-biphenylylmethyl]benzimidazole.

Example 16 a) Analogously to Example 1 a), the two compounds
mentioned in Example 14 b), by reaction with the com-
pounds of the formula $R^3$-X below, give the 2-cyclopro-
pyl-1-[2'-(1H-5-tetrazolyl)-4-biphenylylmethyl]ben-
zimidazoles below:
with methyl bromoacetate:
-5-(1,4,5,6-tetrahydro-1-methoxycarbonylmethyl-4-me-
thyl-6-oxo-3-pyridazinyl)--
-6-(1,4,5,6-tetrahydro-1-methoxycarbonylmethyl-4-
methyl-6-oxo-3-pyridazinyl)-, dihydrate, m.p. 125°;
with N,N-dimethylchloroacetamide:
-5-(1,4,5,6-tetrahydro-1-N,N-dimethyl-carbamoylmeth-
yl-4-methyl-6-oxo-3-pyridazinyl)--
-6-(1,4,5,6-tetrahydro-1-N,N-dimethyl-carbamoylmeth-
yl-4-methyl-6-oxo-3-pyridazinyl)-;
with benzyl bromide:
-5-(1-benzyl-1,4,5,6-tetrahydro-4-methyl-6-oxo-3-pyrid-
azinyl)--
-6-(1-benzyl-1,4,5,6-tetrahydro-4-methyl-6-oxo-3-
pyridazinyl)-
with methyl 2-bromomethylbenzoate:
-5-[1,4,5,6-tetrahydro-1-(2-methoxycarbonyl-benzyl)-4-
-methyl-6-oxo-3-pyridazinyl]--
-6-[1,4,5,6-tetrahydro-1-(2-methoxycarbonyl-benzyl)-4-
methyl-6-oxo-3-pyridazinyl]-, FAB 651 .

b) Analogously to Example 12, dehydrogenation of
the above compounds using Na 3-nitrobenzenesulfonate
in aqueous NaOH solution gives the 2-cyclopropyl-1-
[2'(1H-5-tetrazolyl)-4-biphenylylmethyl]ben-
zimidazoles below (ester groups being hydrolyzed.):
-5-(1-carboxymethyl-1,6-dihydro-4-methyl-6-oxo-3-py-
ridazinyl)--
-6-(1-carboxymethyl-1,6-dihydro-4-methyl-6-oxo-3-
pyridazinyl)-, FAB 559; trihydrate, m.p. >300°.
-5-(1,6-dihydro-1-N,N-dimethyl-carbamoylmethyl-4-m- ethyl-6-oxo-3-pyridazinyl)--
-6-(1,6-dihydro-1-N,N-dimethyl-carbamoylmethyl-4-methyl-6-oxo-3-pyridazinyl)-, FAB 586 -5-(1-benzyl1, 6-dihydro-4-methyl-6-oxo-3-pyridazinyl)- -6-(1-benzyl-1,6-dihydro-4-methyl-6-oxo-3-pyridazinyl)--
-5-[1-(2-carboxybenzyl-1,6-dihydro-4-methyl-6-oxo-3-pyridazinyl]--
-6-[1-(2-carboxybenzyl-1,6-dihydro-4-methyl-6-oxo-3-pyridazinyl]-, FAB 636; m.p. >300°.

Example 17

(a) Analogously to Example 1 (a), but in DMF, there are obtained from 2-cyclopropyl-5- (1,4,5, 6-tetrahydro-6-oxo-3-pyridazinyl)-benzimidazole [obtainable by reaction of 3-(3,4-diaminophenyl)-1,4,5,6-tetrahydro-6-pyridazinone with cyclopropanecarboxylic acid and subsequent cyclization with acetic acid analogously to Example 3] and IIb after conventional working-up (chromatography over silica gel with ethyl acetate/methanol 96:4) in succession 1- (2 '-cyano-biphenylyl-4-methyl ) -2-cyclopropyl-6-(1,4,5,6-tetrahydro-6-oxo-3-pyridazinyl) -benzimidazole (FAB 446), followed by 1-(2'-cyano-biphenylyl-4-methyl)2-cyclopropyl-5-(1,4,5,6-tetrahydro-6-oxo-3-pyridazinyl)-benzimidazole (FAB 446).

(b) Analogously to Example 3 (b), there are obtained from the two compounds obtained according to (a) with trimethyltin azide: 2-cyclopropyl-6- (1,4,5, 6-tetrahydro-6-oxo-3-pyridazinyl)1-[2'-(1H-5-tetrazolyl)-biphenylyl-4-methyl]benzimidazole and 2-cyclopropyl-5-(1,4,5,6-tetrahydro-6-oxo-3-pyridazinyl)-1-[2'-(1H-5-tetrazolyl)-biphenylyl-4-methyl]-benzimidazole.

Example 18

(a) Analogously to Example I (a), but in DMF, there are obtained from 2-cyclopropyl-5- (1,4,5,6-tetrahydro-4,4-dimethyl-6-oxo-3-pyridazinyl)-benzimidazole[obtainable by reaction of 3- (3,4-diaminophenyl)-1,4,5,6'tetrahydro-4,4-dimethyl-6-pyridazinone with cyclopropanecarboxylic acid and subsequent cyclization with acetic acid analogously to Example 3]and IIb after conventional working-up (chromatography over silica gel with ethyl acetate/methanol 96: 4) in succession 1-(2'-cyano-biphenylyl-4-methyl)-2-cyclopropyl-6-(1,4,5,6-tetrahydro-4,4-dimethyl-6-oxo-3-pyridazinyl)-benzimidazole (FAB 474), followed by 1-(2 '-cyano-biphenylyl-4-methyl)-2-cyclopropyl-5-(1,4,5,6-tetrahydro-4,4-dimethyl-6-oxo-3-pyridazinyl)-benzimidazole (FAB 474).

(b) Analogously to Example 3 (b), there are obtained from the two compounds obtained according to (a) with trimethyltin azide: 2-cyclopropyl-6-(1,4,5,6-tetrahydro-4,4-dimethyl-6-oxo-3-pyridazinyl)-1-[2'- (1H-5-tetrazolyl)-biphenylyl-4-methyl]-benzimidazole (m.p. 237°) and 2-cyclopropyl-5- (1,4,5,6-tetrahydro-4,4-dimethyl-6-oxo-3-pyridazinyl)-1-[2'-(1H-5-tetrazolyl)-biphenylyl-4-methyl]-benzimidazole (m.p. 248°).

The following examples relate to pharmaceutical formulations containing active ingredients of formula I or their salts.

Example A: Tablets and coated tablets

Tablets of the following composition are produced by compression in conventional manner and, where required, are provided with a conventional sucrose-based coating:

| | |
|---|---|
| Active ingredient of formula I | 100 mg |
| Microcrystalline cellulose | 278.8 mg |
| Lactose | 110 mg |
| Maize starch | 11 mg |
| Magnesium stearate | 5 mg |
| Finely divided silicon dioxide | 0.2 mg |

Example B: Hard gelatin capsules

Conventional two-part hard gelatin capsules are each filled with

| | |
|---|---|
| Active ingredient of formula I | 100 mg |
| Lactose | 150 mg |
| Cellulose | 50 mg |
| Magnesium stearate | 6 mg |

Example C: Soft gelatin capsules

Conventional soft gelatin capsules are filled with a mixture of 50 mg of active ingredient and 250 mg of olive oil in each case.

Example D: Ampoules

A solution of 200 g of active ingredient in 2 kg of propane-1,2-diol is made up to 10 l with water and filled into ampoules so that each ampoule contains 20 mg of active ingredient.

Example E: Aqueous suspension for oral administration

An aqueous suspension is prepared in conventional manner. The unit dose (5 ml) contains 100 mg of active ingredient, 100 mg of sodium carboxymethyl cellulose, 5 ml of sodium benzoate and 100 mg of sorbitol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A benzimidazole compound of formula I

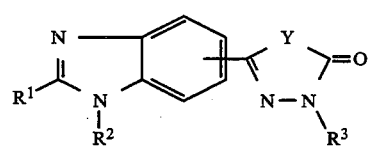

I wherein
$R^1$ is A, $C_pH_{2p}$-($C_{3-7}$-cycloalkyl), OA or SA;
$R^2$ and $R^3$ are in each case, independently,

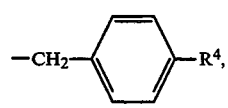

(1)

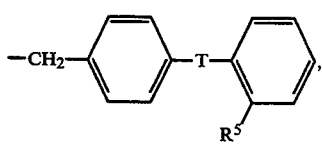

(2)

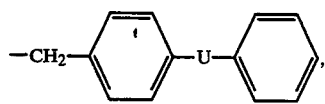

(3)

(4) —C$_{1-10}$-alkyl, —C$_n$H$_{2n}$—COOR, —C$_n$H$_{2n}$—CN, —C$_m$H$_{2m}$—Ar, —C$_m$H$_{2m}$—Het$^2$, —C$_n$H$_{2n}$—1H-5-tetrazolyl, —C$_n$H$_{2n}$—CH=CH—Ar, —C$_n$H$_{2n}$—CO—N(R)$_2$, —C$_m$H$_{2m}$—CO—R, —C$_m$H$_{2m}$—CO—Ar, —C$_n$H$_{2n}$—O—CON(R)$_2$ or —C$_n$H$_{2n}$—NR—CO—N(R)$_2$, or (5) H;

Y is —C(R)$_2$—C(R)$_2$—, —CR=CR— or —C(R)$_2$—S—;

R is, in each case, independently H or A;

R$^4$ is COOR, CN or 1H-5-tetrazolyl;

R$^5$ is COOR, CN, NO$_2$, NH$_2$, NHCOCF$_3$, NHSO$_2$CF$_3$ or 1H-5-tetrazolyl;

T is absent or is —NR—CO—, —CO—NR— or —CH=CH—;

U is —CH=C(COOR)—, —CH=C(CN)—, —CH=C(1H-5—tetrazolyl)—, —O—CH(COOR)— or —NR—CH(COOR)—;

m and p are each 0, 1, 2, 3, 4, 5, 6, 7, 8, 9 or 10;

n is 1, 2, 3, 4, 5, 6, 7, 8, 9 or 10;

A is alkyl having 1-6 C atoms;

Ar is a phenyl or naphthyl group which is unsubstituted or mono- or disubstituted by A, Hal, OH, OA, COOH, COOA, CN, CF$_3$, NO$_2$, NH$_2$, NHA, N(A)$_2$ or combinations thereof;

Het$^2$ is an unsubstituted five- or six-membered heteroaromatic radical having 1 to 3 heteroatoms, said heteroatoms in each case being selected from N, O, and S atoms a substituted five- or six-membered heteroaromatic radical having 1 to 3 heteroatoms, said heteroatoms in each case being selected from N, O, and S atoms, an unsubstituted five- or six-membered heteroaromatic radical having 1 to 3 heteroatoms, said heteroatoms in each case being selected from N, O, and S atoms, wherein said radical is fused with a benzene or pyridine ring, or a substituted five- or six-membered heteroaromatic radical having 1 to 3 heteroatoms, said heteroatoms in each case being selected from N, O, and S atoms, wherein said radical is fused with a benzene or pyridine ring; and Hal is F, Cl, Br or I;

with the provisos that (a) Y is only —C(R)$_2$—C(R)$_2$— or —CR=CR— if R$^1$ is other than —C$_p$H$_{2p}$—(C$_{3-7}$—cycloalkyl), R$^3$ is other than H, or R$^1$ is other than —C$_p$H$_{2p}$—(C$_{3-7}$—cycloalkyl) and R$^3$ is other than H; and (b) at least one of R$^2$ and R$^3$ has one of the meanings (1), (2) or (3); or a physiologically acceptable salt thereof.

2. A compound according to claim 1, wherein said compound is:

(a) 2-butyl-5-[1-(2'-carboxy-biphenylyl-4-methyl)-1,6-dihydro-4-methyl-6-oxo-3-pyridazinyl]benzimidazole or a physiologically acceptable salt thereof;

(b) 2-butyl-1-(2'-carboxy-biphenylyl-4-methyl)-6-(1-carboxymethyl-1,4,5,6-tetrahydro-4-methyl-6-oxo-3-pyridazinyl)-benzimidazole or a physiologically acceptable salt thereof;

(c) 2-butyl-1-(2'-carboxy-biphenylyl-4-methyl)-5-(1-carboxymethyl-1,4,5,6-tetrahydro-4-methyl-6-oxo-3-pyridazinyl)-benzimidazole or a physiologically acceptable salt thereof.

3. A compound according to claim 1, wherein Het$^2$ is an unsubstituted 5- or 6-membered heteroatomic radical having 1-3 heteroatoms, said heteroatoms in each case being selected from N, O and S atoms; a 5- or 6-membered heteroatomic radical having 1-3 heteroatoms which is substituted by 1-2 A groups, said heteroatoms in each case being selected from N, O and S atoms; an unsubstituted 5- or 6-membered heteroatomic radical having 1-3 heteroatoms, said heteroatoms in each case being selected from N, O and S atoms, wherein said radical is fused with a benzene or pyridine ring; or a 5- or 6-membered heteroatomic radical having 1-3 heteroatoms which is substituted by 1-2 A groups, said heteroatoms in each case being selected from N, O and S atoms wherein said radical is fused with a benzene or pyridine ring.

4. A compound according to claim 1, wherein Het$^2$ is:
an unsubstituted 5- or 6-membered heteroatomic radical having 1-3 heteroatoms, said heteroatoms in each case being selected from N, O and S atoms, or
an unsubstituted 5- or 6-membered heteroatomic radical having 1-3 heteroatoms, said heteroatoms in each case being selected from N, O and S atoms, which is fused with a benzene or pyridine ring.

5. A compound according to claim 1, wherein R$^1$ is A, cyclopropyl or.

6. A compound according to claim 1, wherein R$^1$ is A.

7. A compound according to claim 1, wherein R$^2$ is H, 2'-cyano-biphenylyl-4-methyl, 2'-carboxy-biphenylyl-4-methyl, 2'-(1H-5-tetrazolyl)-biphenylyl-4-methyl or p-(2-cyano-2-phenylvinyl)-benzyl.

8. A compound according to claim 7, wherein R$^1$ is A.

9. A compound according to claim 1, wherein R$^3$ is H, carboxymethyl, carboxybenzyl, 2'-cyano-biphenylyl-4-methyl, 2'-carboxy-biphenylyl-4-methyl or 2'-(1H-5-tetrazolyl)-biphenylyl-4-methyl.

10. A compound according to claim 1, wherein R$^3$ is H.

11. A compound according to claim 1, wherein R$^3$ is carboxymethyl.

12. A compound according to claim 1, wherein Y is —CH(CH$_3$)—CH$_2$— or —C(CH$_3$)=CH—.

13. A compound according to claim 1, wherein R$^1$ is C$_p$H$_{2p}$—(C$_{3-7}$-cycloalkyl) wherein cycloalkyl is cyclopropyl, cyclobutyl, cyclopentyl, cyclohexyl, cycloheptyl, 1-methylcyclopropyl, 2-methylcyclopropyl, 1-methylcyclopentyl, 2-methylcyclopentyl, 3-methylcyclopentyl, 1-methylcyclohexyl, 2-methylcyclohexyl, 3-methylcyclohexyl or 4-methylcyclohexyl.

14. A compound according to claim 1, wherein T is absent.

15. A compound according to claim 1, wherein R is, in each case, independently, H, CH$_3$ or C$_2$H$_5$.

16. A pharmaceutical composition comprising of a pharmaceutically acceptable carrier and a compound of claim 1.

17. A pharmaceutical composition according to claim 15, wherein said compound is administered in an amount of 1 mg-1 g.

18. A method of treating or prophylaxis of angiotensin(II)-dependent diseases or conditions, comprising administering an effective amount of a compound according to claim 1.

19. A method according to claim 18, wherein said compound is administered in a daily dosage of 0.1-100 mg/kg.

20. A method according to claim 18, wherein said disease is angiotensin(II)-dependent hypertension.

21. A method according to claim 19, wherein said disease is angiotensin(II)-dependent hypertension.

22. A compound according to claim 1, wherein $R^2$ is

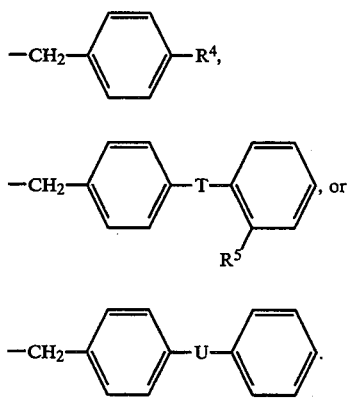

23. A compound according to claim 1, wherein $R^3$ is

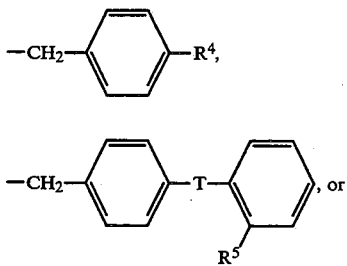

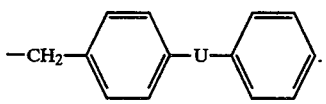

24. A compound according to claim 1, wherein $Het^2$ is 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, or else preferably 1,2,3-triazol-1-, -4- or -5-yl, 1,2,4-triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 2,1,5-thiadiazol-3- or -4-yl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6-or 7-indolyl, 1-, 2-, 3-, 4-, 5-, 6- or 7 -isoindolyl, 1-, 2 -, 4 - or 5 -benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7 -benzothiazolyl, 2-, 4-, 5-, 6- or 7-benzisothiazolyl, 4 -, 5-, 6 - or 7 -benz-2 - 1,3 -oxadiazolyl, 2 -, 3-, 4-, 5-, 6-, 7-or 8-quinolyl, 1-, 3-, 4-, 5-, 6-, 7- or 8-isoquinolyl, 3-, 4-, 5-, 6-, 7-or 8-cinnolyl, 2-, 4-, 5-, 6-, 7- or 8-quinazolyl, 1H-1-, -2-, -5-, -6- or -7-imidazo[4,5-b ]pyridyl, 3H-2-, -3-, -5-, -6- or -7-imidazo[4,5-b ]pyridyl, 1H-1-, -2-, -4-, -6- or -7imidazo[4,5-c ]pyridyl or 3H-2-, -3-, -4-, -6- or -7-imidazo[4,5-c]pyridyl, 3-, 4-, or 5-methyl-2-furyl, 2,-4- or 5-methyl-3-furyl, 2,4-dimethyl-3-furyl, 3-, 4- or 5-methyl-2-thienyl, 3-methyl-5-tert-butyl-2-thienyl, 2-, 4- or 5-methyl-3-thienyl, 2- or 3-methyl-1-pyrrolyl, 1-, 3-, 4 - or 5-methyl-2 -pyrrolyl, 3,5-dimethyl-4-ethyl-2-pyrrolyl, 2-, 4- or 5-methyl-1-imidazolyl, 4-methyl-5-pyrazolyl, 4- or 5-methyl-3-isoxazolyl, 3- or 5-methyl-4-isoxazolyl, 3- or 4-methyl-5-isoxazolyl, 3,4-dimethyl-5-isoxazolyl, 4- or 5-methyl-2-thiazolyl, 4-or 5-ethyl-2-thiazolyl, 2- or 5-methyl-4-thiazolyl, 2- or 4-methyl-5-thiazolyl, 2,4-dimethyl-5-thiazolyl, 3-, 4-, 5- or 6-methyl-2-pyridyl, 2-, 4-, 5- or 6-methyl-3-pyridyl, 2- or 3-methyl-4-pyridyl, 4-methyl-2-pyrimidinyl, 4,6-dimethyl-2-pyrimidinyl, 2-, 5- or 6-methyl-4-pyrimidinyl, 2,6-dimethyl-4-pyrimidinyl, 3-, 4-, 5-, 6- or 7-methyl-2-benzofuryl, 2-ethyl-3-benzofuryl, 3-, 4-, 5-, 6- or 7 -methyl-2-benzothienyl, 3-ethyl-2-benzothienyl, 1-, 2-, 4-, 5-, 6- or 7-methyl-3-indolyl, 1-methyl-5- or 6-benzimidazolyl, 1-ethyl-5- or 6-benzimidazolyl.

* * * * *

UNITED STATES PATENT AND TRADEMARK OFFICE
CERTIFICATE OF CORRECTION

PATENT NO. : 5,401,738
DATED : March 28, 1995
INVENTOR(S) : Werner MEDERSKI et al.

It is certified that error appears in the above-indentified patent and that said Letters Patent is hereby corrected as shown below:

Claim 5; column 22, line 38: After cyclopropyl delete "or" and after "A", insert --or--.

Signed and Sealed this

Eleventh Day of July, 1995

Attest:

BRUCE LEHMAN

Attesting Officer  Commissioner of Patents and Trademarks